United States Patent
Lansing et al.

(10) Patent No.: US 12,427,522 B2
(45) Date of Patent: Sep. 30, 2025

(54) INCUBATION CASSETTE FOR RECEIVING A MICROPLATE AND MICROPLATE READER

(71) Applicant: TECAN TRADING AG, Mannedorf (CH)

(72) Inventors: Manfred Lansing, Salzburg (AT); Tobias Sawetzki, Bischofswiesen (DE); Nicole Eggenhofer, Kuchl (AT)

(73) Assignee: TECAN TRADING AG, Mannedorf (CH)

( * ) Notice: Subject to any disclaimer, the term of this patent is extended or adjusted under 35 U.S.C. 154(b) by 0 days.

(21) Appl. No.: 18/591,107

(22) Filed: Feb. 29, 2024

(65) Prior Publication Data

US 2024/0198345 A1    Jun. 20, 2024

Related U.S. Application Data

(62) Division of application No. 17/125,185, filed on Dec. 17, 2020, now Pat. No. 11,958,051.

(30) Foreign Application Priority Data

Dec. 20, 2019   (EP) .................................. 19 218 978

(51) Int. Cl.
 B01L 3/00 (2006.01)
 B01L 9/00 (2006.01)
 (Continued)

(52) U.S. Cl.
 CPC ............ B01L 3/5085 (2013.01); B01L 9/523 (2013.01); G01N 21/59 (2013.01);
 (Continued)

(58) Field of Classification Search
 CPC ............ G01N 35/028; G01N 21/3577; G01N 21/6452; G01N 21/253; G01N 21/59;
 (Continued)

(56) References Cited

U.S. PATENT DOCUMENTS 4,800,164 A * 1/1989 Bisconte ................. C12M 41/48
  435/286.4
6,097,025 A * 8/2000 Modlin ................... G01N 21/76
  250/227.22

(Continued)

FOREIGN PATENT DOCUMENTS

CH           706811 A1    2/2014
EP         3270120 A1    1/2018
(Continued)

*Primary Examiner* — Shogo Sasaki
(74) *Attorney, Agent, or Firm* — Notaro, Michalos & Zaccaria P.C.

(57) ABSTRACT

An incubation cassette is disclosed for reducing liquid evaporation from wells of a microplate. A frame has a central first opening surrounded by an inner wall having dimensions designed for the placement of a microplate therein and an outer wall which extends substantially parallel to the inner wall. The outer wall adjoins the inner wall via an intermediate bottom such that a liquid reservoir is formed thereby. The liquid reservoir surrounds the first central opening. At least a portion of the incubation cassette that forms the liquid reservoir has a transparent portion. A microplate reader has a housing and a transport support which can be pulled out of the housing. The transport support has a bearing surface for placement of a microplate having a plurality of wells or such an incubation cassette, and a controller adapted to control a method for reducing liquid evaporation from wells of the microplate.

19 Claims, 12 Drawing Sheets

(51) Int. Cl.
*G01N 21/59* (2006.01)
*G01N 21/64* (2006.01)

(52) U.S. Cl.
CPC ...... *G01N 21/6452* (2013.01); *B01L 2200/06* (2013.01); *B01L 2200/142* (2013.01); *B01L 2300/0829* (2013.01)

(58) Field of Classification Search
CPC ......... G01N 21/359; G01N 2021/0143; G01N 2021/6484; B01L 9/523; B01L 3/50853; B01L 3/5085; B01L 2300/0829; B01L 2200/06; B01L 2200/142; C12M 23/38; C12M 23/12; G01F 23/292
See application file for complete search history.

(56) References Cited

U.S. PATENT DOCUMENTS

| | | | |
|---|---|---|---|
| 2013/0255374 A1* | 10/2013 | Oura | G01F 23/292 |
| | | | 73/293 |
| 2014/0113360 A1 | 4/2014 | Lee | |
| 2016/0003859 A1* | 1/2016 | Wenczel | G01N 35/04 |
| | | | 422/561 |
| 2016/0199838 A1* | 7/2016 | Handique | B01L 3/502761 |
| | | | 435/287.2 |

FOREIGN PATENT DOCUMENTS

| | | | |
|---|---|---|---|
| EP | 2943797 B1 | 10/2018 | |
| WO | 2016/203320 A2 | 12/2016 | |

* cited by examiner

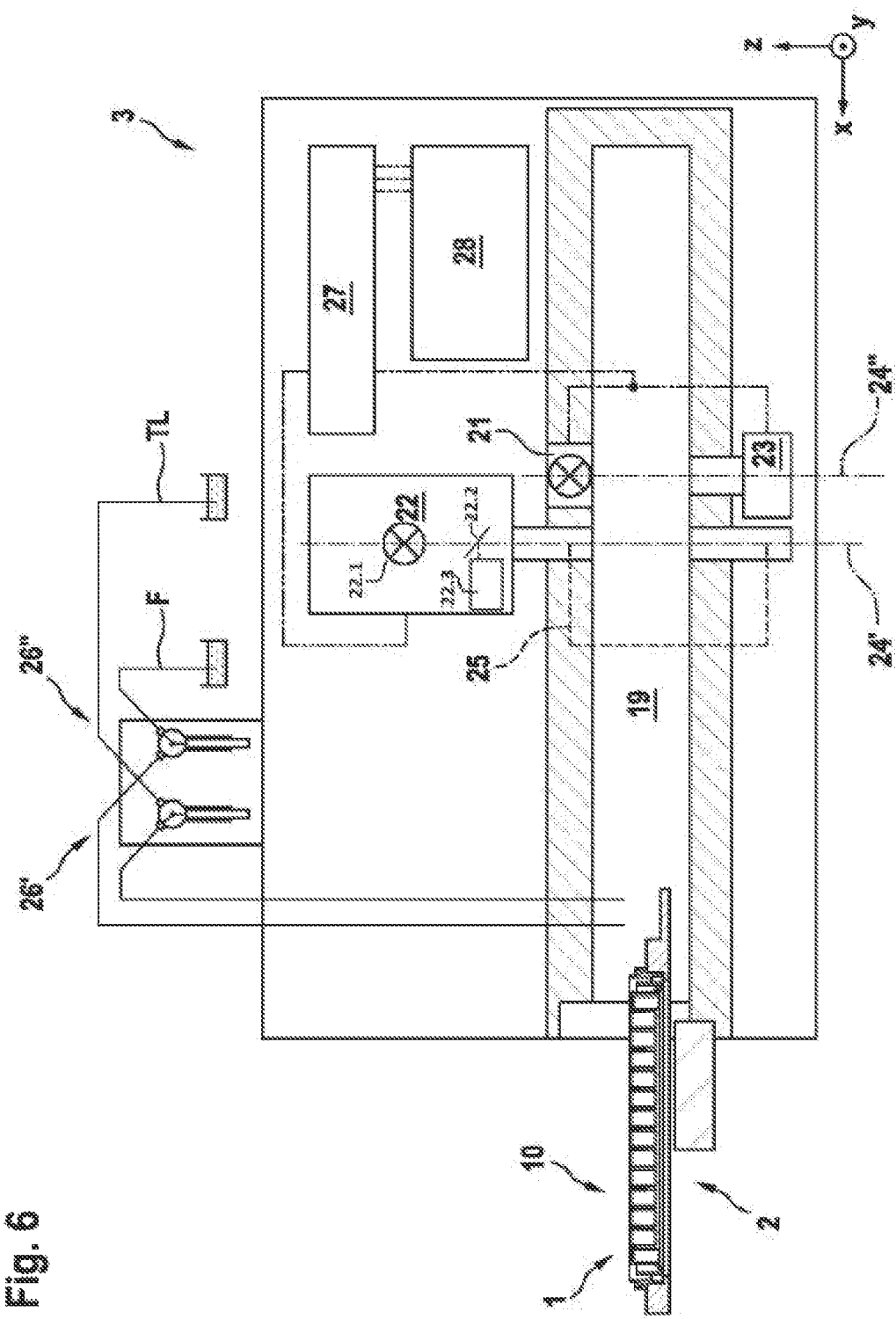

INCUBATION CASSETTE FOR RECEIVING A MICROPLATE AND MICROPLATE READER

CROSS-REFERENCE TO RELATED APPLICATIONS

This application is a divisional application of co-pending U.S. patent application Ser. No. 17/125,185 filed on Dec. 17, 2020, which claims priority to European patent application Ser. No. 19 218 978.5 filed on Dec. 20, 2019, the contents of each of which are incorporated herein in their entirety.

FIELD

The invention relates to a method for reducing liquid evaporation from wells of a microplate, more specifically to an incubation cassette for receiving a microplate and to a microplate reader.

BACKGROUND

Microplate readers, by which the contents of one or more wells of a microplate can be optically assayed or analysed, have been known for a long time. In connection with the present invention, a microplate is any multi-well plate that has a plurality of wells or containers which are arranged for example in an array. Especially preferred microplates have at least approximately the dimensions and the footprint of a microplate according to the SBS standard, as published by the American National Standards Institute (ANSI). Known microplates are, for example, those standard microplates having wells that are equipped with a round bottom, flat bottom or V-shaped bottom. One common feature of all these standard microplates having greatly varying well shapes is that the axial spacing of the wells, which are in each case arranged in an array, is also standardized (cf. ANSI_SBS 1-2-3-4-2004 standard for microplate dimensions from the year 2006). This axial spacing is for example 18 mm in the case of 24-well (4×6) plates, 9 mm in the case of 96-well (8×12) plates, 4.5 mm in the case of 384-well (16×24) plates, and 2.25 mm in the case of 1536-well (32×48) plates. The height of a standard microplate may vary greatly depending on the type and is typically between 10.4 mm (for example 1536 V-bottom deep well plate) and 44 mm (for example 96-well Masterblock from Greiner).

Known microplate readers are equipped with suitable light sources and/or detectors for assaying samples, or samples provided with test solution, in the wells of microplates based on the absorption, fluorescence and/or luminescence thereof. By way of example, the samples are located in a test solution which is exposed to environmental influences. Particularly in the case of long-term experiment series using cell cultures in the wells, which are typically carried out in stand-alone microplate readers over hours or even days and possibly also at elevated temperatures compared to room temperature, evaporation problems may arise for the samples or the test solution containing the samples. The evaporation of the test solution leads to a thickening and thus to a change in the concentration of buffer substances and molecules to be assayed (analytes). This changes for example the growth conditions for cell-based experiments and/or the reaction of cells to experiment-induced influences. It has also been observed that the test solution of wells arranged in the corners of a standard microplate suffers from such evaporation problems more than that of wells arranged in the middle of a microplate. This in turn means that the thickening does not occur in a manner distributed homogeneously across all wells of a microplate, but instead leads to differences, and thus to non-comparable results, within the same experiment series.

Devices for preventing or reducing such evaporation problems are known from the prior art. For instance, the patent EP 2943797 B1 discloses an incubation cassette for reducing liquid evaporation from wells of a microplate, wherein the incubation cassette comprises a frame for receiving a microplate. The incubation cassette also provides a reservoir which can be filled with liquid, said reservoir being in the form of a liquid channel which surrounds the inserted microplate. As a result, the atmosphere in the immediate vicinity of the wells of the microplate is enriched accordingly, so that any thickening of the sample liquid caused by evaporation can be delayed.

In the prior art, however, the liquid in the liquid channel may evaporate completely, as a result of which the atmosphere in the immediate vicinity of the microplate wells is no longer enriched. The liquid level or amount of liquid in the liquid channel must therefore be checked frequently, and the liquid must be topped up manually in order to maintain the functionality. The checking and manual topping-up of the liquid channel take a lot of time and effort. Another disadvantage is that the liquid channel cannot be topped up with liquid during some measurements, particularly in the case of long-term measurements, without disrupting the experiment.

SUMMARY

The object of the present invention is therefore to propose an incubation cassette and a microplate reader that enable reducing liquid evaporation from wells of a microplate, in which the disadvantages known from the prior art are eliminated.

This object is achieved by an incubation cassette and a microplate reader according to the claims.

A method for reducing liquid evaporation from wells of a microplate comprises:
a) providing the microplate,
b) adding a sample to at least one of the wells of the microplate,
c) pushing the microplate or an incubation cassette equipped with the microplate into a microplate reader,
d) injecting a liquid into a liquid reservoir which is provided in the microplate and/or in the incubation cassette,
e) carrying out measurements on the samples in the respective wells,
f) measuring a liquid level in the liquid reservoir of the microplate and/or of the incubation cassette,
g) re-injecting the liquid into the liquid reservoir of the microplate and/or of the incubation cassette if the liquid level is below a predetermined threshold value,
h) repeating steps e) to g) until a predetermined number of measurement cycles is reached,
i) pulling the microplate or the incubation cassette equipped with the microplate out of the microplate reader.

The order of the steps of the method can be changed. By way of example, the liquid can also be injected into the liquid reservoir of the microplate and/or of the incubation cassette outside of the microplate reader, that is to say before the microplate or the incubation cassette equipped with the microplate is pushed into the microplate reader.

The incubation cassette according to the invention for reducing liquid evaporation from wells of a microplate comprises a frame for receiving a microplate having wells, wherein the frame comprises a central first opening which is surrounded by an inner wall and the dimensions of which are designed for the placement of a microplate therein, and the frame comprises an outer wall which extends substantially parallel to the inner wall and which adjoins the inner wall via an intermediate bottom such that a liquid reservoir for holding a liquid is formed by the two walls and the intermediate bottom, said liquid reservoir surrounding the first central opening, wherein at least a portion of the incubation cassette that forms the liquid reservoir is provided at least in part with at least one transparent portion.

Advantages of the invention include:

The monitoring of the liquid level in the liquid reservoir of the microplate and/or of the incubation cassette can be carried out in an automated manner, regardless of the duration of the experiment, by measuring samples in the wells of the microplate at intervals.

Due to the transparent portion of the incubation cassette and/or the transparent portion of the microplate placed in the incubation cassette, these are optically accessible from below so that optical measurements can be used to determine the liquid level in the liquid reservoir. The light for the respective optical measurement passes through the respective transparent portion.

The liquid reservoir of the microplate and/or of the incubation cassette can be filled and/or topped up with liquid manually or in an automated manner by an injector as soon as it is detected that the liquid level in the liquid reservoir is below a predefined liquid level. As a result, the liquid reservoir reliably remains filled with liquid.

The re-injection of the liquid into the liquid reservoir of the microplate and/or of the incubation cassette can be carried out by an injector which is already included in the microplate reader. The samples or the samples provided with test solution are thus advantageously exposed to reduced fluctuations in temperature and/or atmosphere.

To monitor the liquid level in an automated manner, at least one optical measuring device can be used, in particular an absorbance measuring device.

The transparent portion of the microplate or incubation cassette enables light to impinge on the liquid from below in order to optically measure the liquid level by means of an absorbance measurement for example.

The appropriate device for optically measuring the liquid level in the liquid reservoir of the microplate and/or of the incubation cassette may already be included in the microplate reader, such as for example a device for optically analysing samples in the wells of the microplate, in particular for measuring absorbance. This provides a saving in terms of cost and space since use can be made of a device that is already included in the microplate reader.

By determining the light absorbance, the liquid level of the liquid in the liquid reservoir of the microplate or incubation cassette can be precisely determined. In general, the amount of light absorbed by the liquid makes it possible to deduce the concentration of the liquid and/or the liquid level.

The incubation cassette is dimensioned and designed such that it can easily be inserted into the transport support of a microplate reader (manually or using robotic means) and can also easily be removed again from said transport support (manually or using robotic means).

To shield the enriched atmosphere from the surrounding environment, a lid can be placed onto the incubation cassette. This lid can be lifted off and placed back on again inside the microplate reader, so that the microplate wells are freely accessible for the time required to perform all necessary actions. When using a microplate without an incubation cassette, a lid can also be placed onto the microplate.

The gas exchange between the microplate wells and the surrounding environment, which is necessary for cell cultures and for cell-based experiments, can be assisted by the lid of the incubation cassette or the lid of the microplate being lifted off sporadically by the operator, by a robot or by a suitable device in the microplate reader itself.

Microplates of any type can be placed into the incubation frame or into the incubation cassette, preference being given to standard microplates according to the ANSI_SBS 1-2-3-4-2004 standard. There is thus no need to use special microplates in order to carry out experiments using cell cultures or cell-based experiments.

Due to the liquid in the reservoir of the incubation cassette and/or microplate and the possibility for the reservoir to be topped up in an automated manner, long-term experiments even at elevated temperature (for example at 37° C.) can advantageously be carried out in a microplate reader.

BRIEF DESCRIPTION OF THE DRAWINGS

The invention will be shown by way of example with the aid of schematic figures in the drawing. The figures are intended to document selected embodiments of the subject matter of the invention, but do not limit the scope of the present invention. In the figures:

FIG. 6 shows a vertical section through a microplate reader, in which a transport support with an incubation cassette placed thereon and a microplate placed in the latter is pulled out;

DETAILED DESCRIPTION

Figure 1:
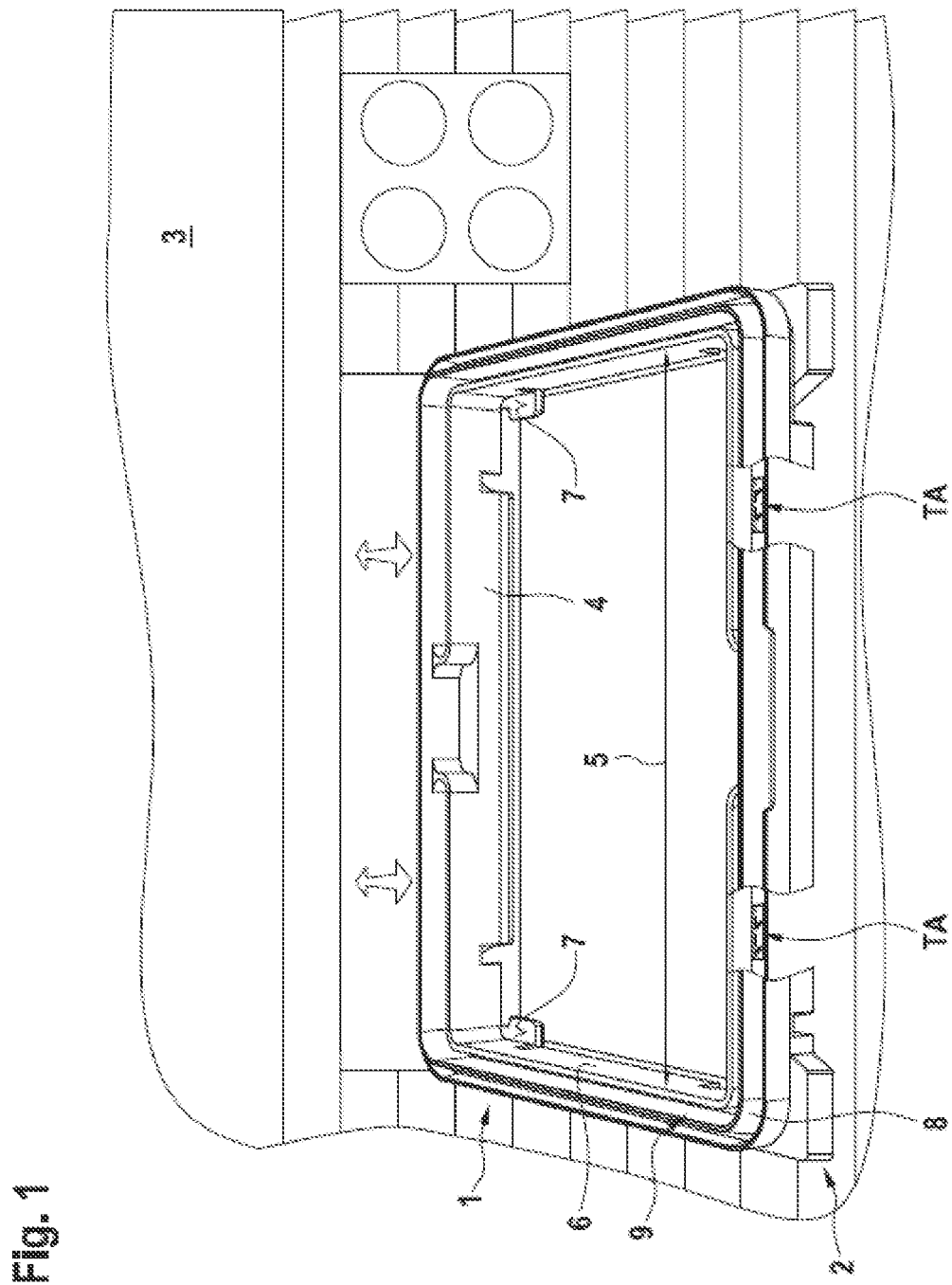
FIG. 1 shows a view of an incubation cassette, with the lid removed, on a transport support of a microplate reader, the incubation cassette being provided with transparent portions.

FIG. 1 shows an embodiment of an incubation cassette 1 according to the invention, which is placed onto a transport support 2 of a microplate reader 3 for transporting the incubation cassette 1. A microplate (not shown), for example a standard microplate, may in turn be inserted into the incubation cassette 1.

The incubation cassette 1 according to the invention comprises a frame 4, onto which a lid can be placed (not shown). The frame 4 comprises a central first opening 5, the dimensions of which are designed for fully placing the microplate therein. The central first opening 5 is surrounded by a preferably substantially vertical inner wall 6, wherein a plurality of substantially horizontal support surfaces 7 are arranged at least in part preferably at the lower end thereof. Said support surfaces 7 serve to support the microplate placed therein (not shown). The frame 4 of the incubation cassette 1 additionally comprises an outer wall 8 which preferably extends substantially parallel to the inner wall 6 and adjoins the inner wall 6 via an intermediate bottom such that a channel, also referred to as a liquid reservoir 9, for holding a liquid is formed by the two walls 6, 8 and the intermediate bottom, said channel surrounding the central first opening 5 (see also FIGS. 3A, 5A, B).

The liquid reservoir 9 is provided in part with at least one transparent portion TA. In other words, at least a portion of the incubation cassette 1 that forms the liquid reservoir 9, preferably the intermediate bottom, is provided at least in part with at least one transparent portion TA. As used here, portions of the liquid reservoir 9 comprise the inner wall 6, the outer wall 8 and/or the intermediate bottom. The transparent portion TA is arranged such that it is in contact with the liquid held in the liquid reservoir 9. In the example shown, and with preference, the transparent portion TA is arranged in the intermediate bottom. Although not shown, the transparent portion TA may be arranged in at least one of the walls 6, 8. The transparent portion TA contains an optically transparent material, which may be optically transparent to light for example from a measuring device for measuring the absorbance of the liquid and thus for determining an optical path length or a level of the liquid that is held. The transparent portion TA thus makes it possible for the amount of liquid or the liquid level in the liquid reservoir 9 to be monitored by means of optical measurement. The respective light for the optical measurement passes through the transparent portion TA from below the incubation cassette 1. The optical measurement can be carried out in an automated manner, namely regardless of the duration of a respective measurement or rather analysis of samples in wells of a microplate.

Figure 2A:
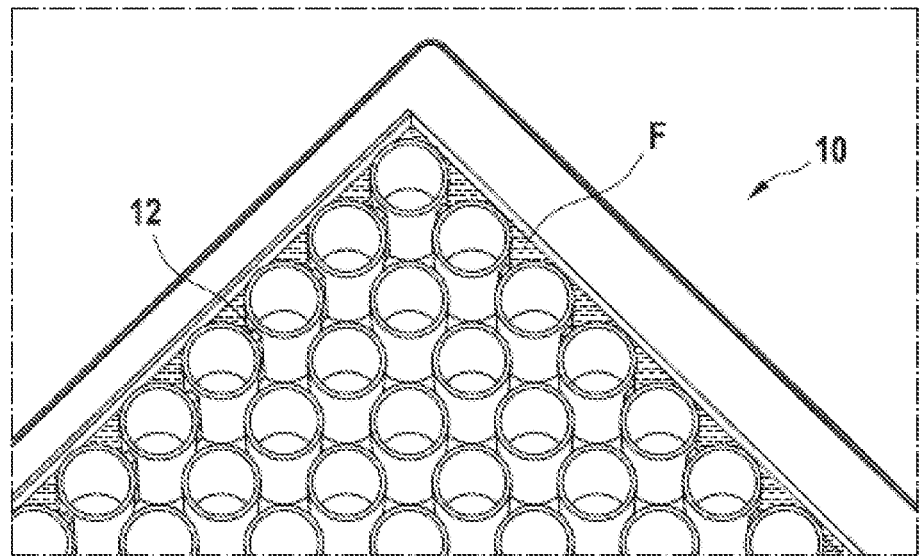
FIGS. 2A, B show detail views of a microplate with differently filled liquid reservoirs.
Figure 2B:
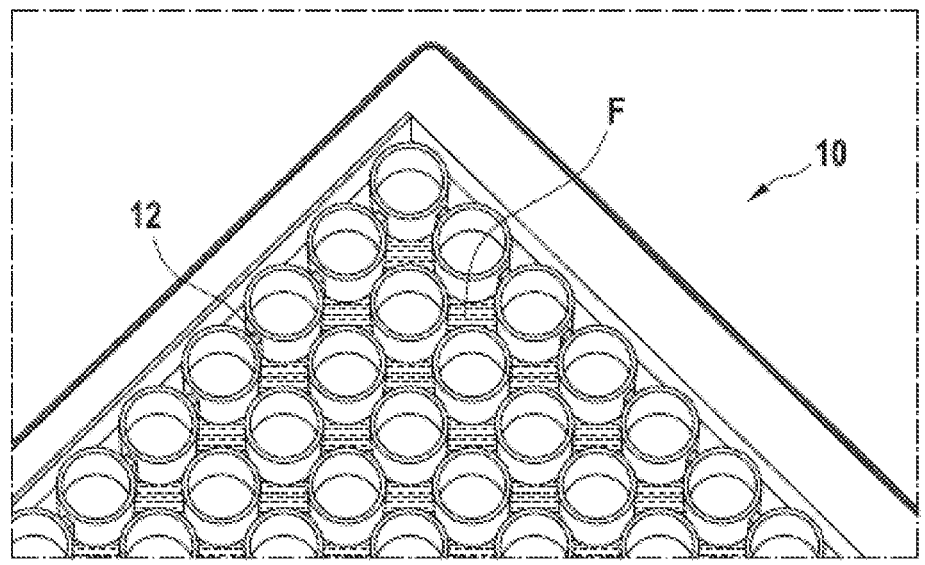

FIGS. 2A, B show detail views of a microplate 10. The microplate 10 contains a plurality of wells, which project upwards from the bottom of the microplate 10 and are open at the top. The microplate 10 is in turn bounded towards the outside by a wall. The intermediate space thus formed forms a reservoir, also called a liquid reservoir, for holding liquid F. In the microplate 10 shown in the figures, the outer wells extending parallel to the wall are connected by webs 12. These webs 12 divide the liquid reservoir into two sub-reservoirs. As can be seen in the figures, a first sub-reservoir is located in the portion of the microplate 10 between the webs 12 (and outer wells) and the wall and is shown filled with liquid F in FIG. 2A. Another sub-reservoir is formed by the remaining (inner) portion of the microplate 10 and is shown filled with liquid F in FIG. 2B. Although not shown, both sub-reservoirs may also be filled with liquid F. The microplate 10 may be formed entirely or partially of transparent material.

Figure 3A:
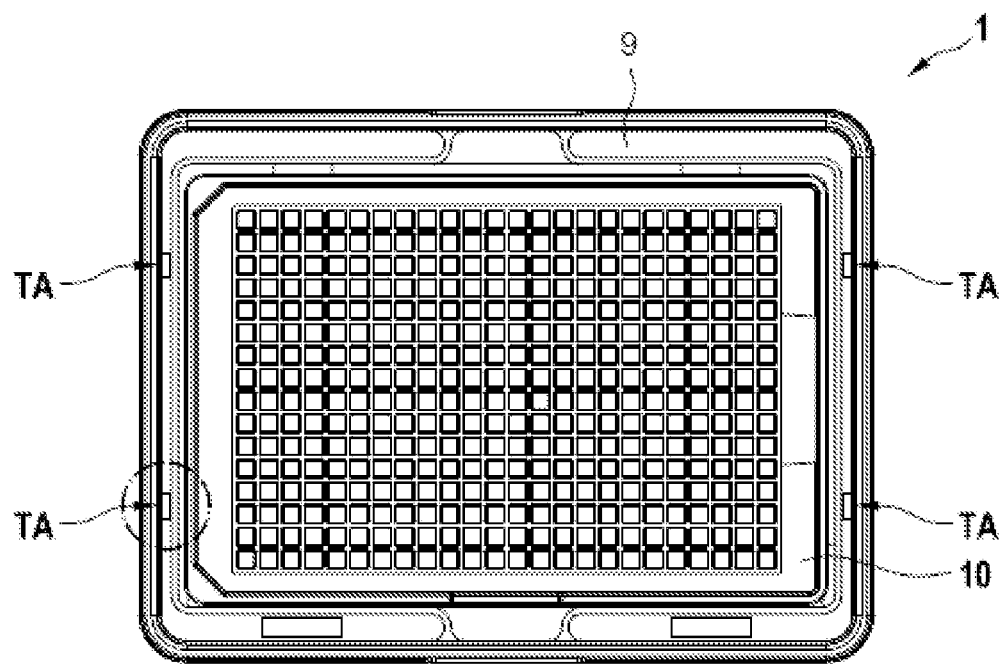
FIGS. 3A, B show a view of a frame of an incubation cassette with a microplate placed therein, in a view from above, and a detail view of a transparent portion of the frame of the incubation cassette.
Figure 3B:
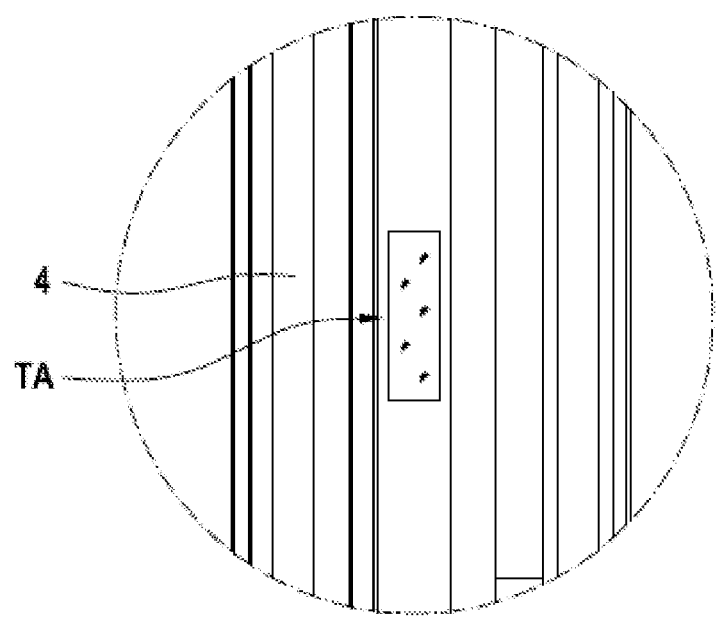

FIG. 3A shows a view of a frame 4 of an incubation cassette 1 with a microplate 10 placed therein (for example a 384-well standard microplate) in a view from above, and FIG. 3B shows a detail view of a transparent portion TA of the frame 4 of the incubation cassette 1. In the region of the liquid reservoir 9 (see also the view in FIG. 1), the frame 4 of the incubation cassette 1 is provided with, for example, six transparent portions TA, through which optical measurements for determining the liquid level in the liquid reservoir 9 of the incubation cassette 1 can be carried out (from below). The microplate 10 itself may be completely transparent so that, in addition or as an alternative, a liquid level of a liquid held in the liquid reservoir of the microplate 10 can be detected therethrough.

Figure 4:
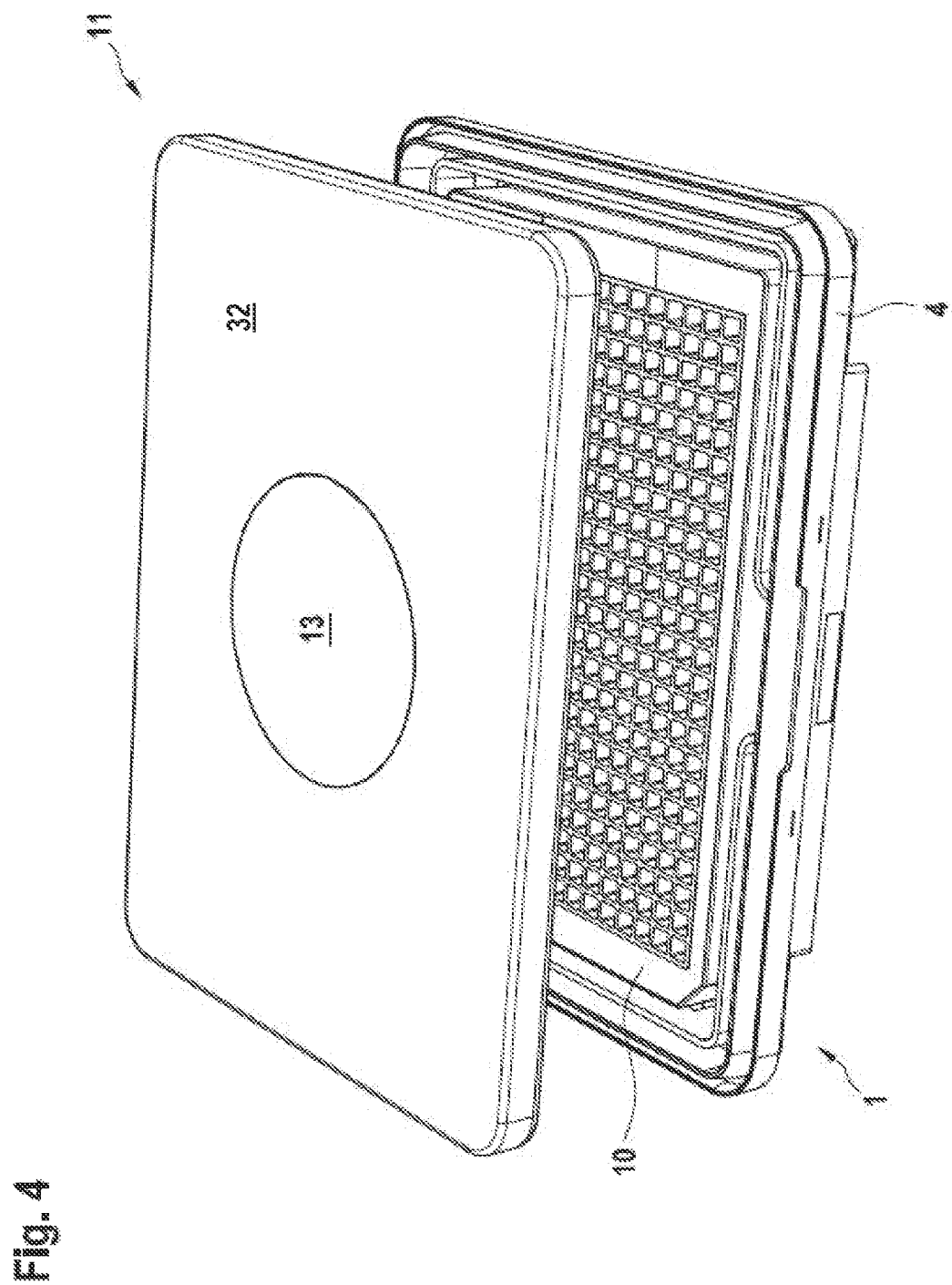
FIG. 4 shows a perspective view of a frame of an incubation cassette with a microplate placed therein, the lid of the microplate having been partially lifted off.

FIG. 4 shows a perspective view of a frame 4 of an incubation cassette 1 with a microplate 10 placed therein, with a lid 11 that has been partially lifted off. The lid 11 of the incubation cassette 1 serves to cover the frame 4 with the microplate 10 placed therein. The lid 11 can be placed on or lifted off inside or outside a microplate reader (not shown), manually or by means of a robot. The lid 11 that is shown comprises a panel 32 having a magnetizable surface 13, which may cover only part of the panel 32. Alternatively, a plurality of such small magnetizable surfaces or a single large magnetizable surface may be provided, which covers at least approximately the entire panel 32. The magnetizable surface 13 may be selected from a group comprising a self-adhesive metal foil, an overmoulded metal plate and a metal plate applied by gluing, and wherein the metal may comprise: iron, nickel, and alloys thereof. A microplate reader may comprise a magnet device, integrated in the housing, for lifting off and placing on the lid 11 of the incubation cassette 1 placed on a transport support. In an alternative example, the lid 11 may be lifted off and placed on by means of a gripper or suction cup (not shown). The lid 11 is preferably made of a chemically inert plastic and is produced for example by injection moulding.

Figure 5A:
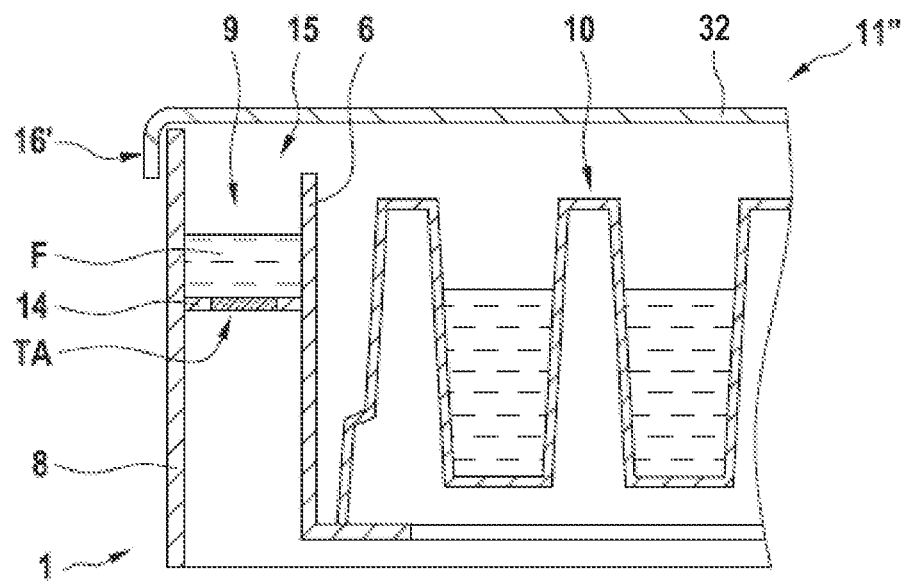
FIGS. 5A, B show partial vertical sections through a covered incubation cassette in different embodiments, each with a schematically shown transparent portion.

FIGS. 5A, B each show schematic partial vertical sections through an incubation cassette 1, covered by a lid 11'; 11", with an inserted microplate 10. The inner wall 6 is connected to the outer wall 8 via an intermediate bottom 14. The outer wall 8, the intermediate bottom 14 and the inner wall 6 define the liquid reservoir 9, into which the liquid F can be filled. As shown schematically in FIGS. 5A, B, the intermediate bottom 10 is provided with the transparent portion TA, through which light can pass for the optical measurement, for example from a suitable measuring device (not shown). In both embodiments shown, the liquid reservoir 9 of the incubation cassette 1 is filled with liquid F. The liquid level of said liquid F can be measured and/or monitored through the transparent portion TA.

In the incubation cassettes 1 shown here, the inner wall 6 may comprise lowered regions 15 so that, when the lid 11'; 11" is placed on, each lowered region 15 connects the microplate 10 to the liquid reservoir 9 surrounding it. It may be provided that the inner wall 6 of the incubation cassette 1 is consistently of reduced height compared to the outer wall 8 so that, when the lid 11'; 11" is placed on, a circumferential gap connects the microplate 10 to the liquid reservoir 9 surrounding it. This results in a continuous gas atmosphere above the liquid reservoir 9 and above the wells of the microplate 10.

The incubation cassette 1 is designed such that light for the optical measurement can pass through the transparent portion TA from below in an unhindered manner. In other words, there should be no portions which could block in the downward direction an optical axis that extends through the respective transparent portion TA. The incubation cassette 1 is preferably made of a chemically inert plastic and is produced for example by injection moulding. The transparent portion(s) TA may be formed in one piece with the incubation cassette 1. The lid 11' of the incubation cassette 1, which is shown in FIG. 5A, comprises a substantially flat panel 32 and a downwardly projecting circumferential edge 16' which is preferably integrally formed on said panel 32. By virtue of this edge 16', the lid 11' can be placed on and lifted off in a reliable and centered manner, without being displaced for example in the event of a sideways displacement of the incubation cassette 1.

Figure 5B:
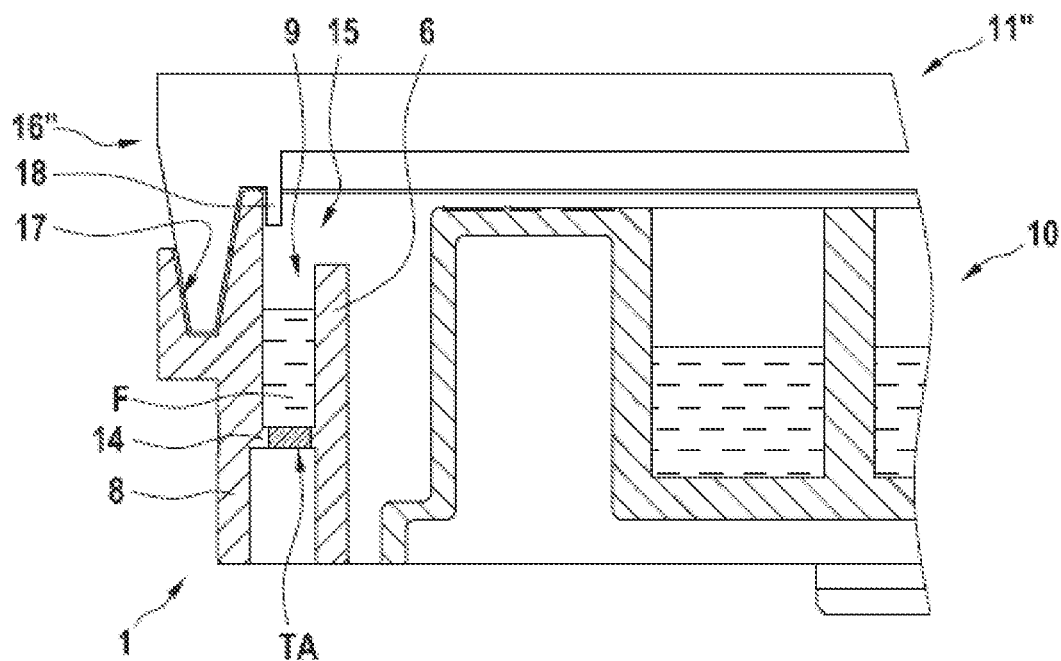

FIG. 5B shows an example of an assembly consisting of an incubation cassette 1 and a lid 11" placed thereon, wherein the lid 11" comprises a downwardly projecting circumferential edge 16" which engages in a circumferential cutout 17 integrally formed on the incubation cassette 1. A downwardly projecting circumferential web 18 may also be integrally formed on the lid 11", which web can abut with a surface against the outer wall 8 of the incubation cassette 1. The lid 11" can thus further be placed on and lifted off in a reliable and centeredmanner, without being displaced for example in the event of a sideways displacement of the incubation cassette 1. Reliable centring of the lid 11" on the incubation cassette 1 is achieved. At the same time, a lid 11" that has been placed on is prevented from slipping on the incubation cassette 1.

FIG. 6 shows a vertical section through a microplate reader 3 for pushing an incubation cassette 1 into a measurement chamber 19, wherein a microplate 10, for example a 96-well standard microplate, is placed in the incubation cassette 1. Although not shown, the incubation cassette 1 may be covered by a lid. The microplate 10 comprises wells which contain, for example, biological structures. In connection with the present invention, the term "biological structures" encompasses: tissue parts, for example of humans, animals or plants; cell cultures or parts thereof; individual cells; cell organelles; macromolecules such as nucleic acids or proteins, and single molecules such as nucleotides, amino acids, hormones and metabolites.

The microplate reader 3 comprises the transport support 2 for holding the incubation cassette 1. The transport support 2 is preferably able to be pulled out of the measurement chamber 19 of the microplate reader 3 to such an extent that the incubation cassette 1 can be placed onto the transport support 2 and/or lifted off the latter manually or by means of a microplate handling robot (not shown). Here, the transport support 2 is shown already partially inserted because clearly the microplate 10 and the incubation cassette 1 surrounding the latter are being pushed into the microplate reader 3. While the incubation cassette 1 is being pushed in or pulled out, a flap is open, which flap in the closed state can preferably close the measurement chamber 19 in a light-impermeable and/or gas-impermeable manner so that no light from the surrounding environment that might influence the experiments can enter the measurement chamber 19 and/or the gas concentration in the measurement chamber 19 can be reliably regulated regardless of the surrounding environment.

Besides holding the incubation cassette 1 equipped with the microplate 10, said transport support 2 also serves to position the microplate 10 having the wells containing the biological structures (for example metabolites, macromolecules, cells or cell cultures) with respect to light sources 21, 22.1 and with respect to measuring devices 22.3, 23 of the microplate reader 3 and/or with respect to the optical axes 24', 24" of the measuring devices 22.3, 23. The light sources 21, 22.1 serve for example to bring about an interaction between at least one of these light sources 21, 22.1 and biological structures in particular wells of the microplate 10, and to bring about or generate a measurable signal. Such signals comprise for example fluorescence emission, luminescence emission, reflected light and/or transmitted light.

In the exemplary embodiment shown, the microplate reader 3 contains a fluorescence module 22 having a first light source 22.1 including a wavelength selection device (not shown), for example a monochromator or wavelength filter, for irradiating a sample (excitation light) along the first optical axis 24'. The fluorescence module 22 additionally contains a semi-transparent or dichroic mirror 22.2 for coupling the light reflected back from the sample (emission light) out of the path of the excitation light (=first optical axis 24'). By way of the mirror 22.2, the emission light is directed towards a first measuring device 22.3. In the fluorescence top reading mode, a sample in a well is irradiated directly from above by the fluorescence module 22, and the emission light is reflected back upwards by the sample. In the bottom reading mode, the excitation light is directed by way of a light guide 25 below the microplate, and the sample is irradiated from below through the bottom of a respective well. The emission light is reflected back downwards by the sample and is directed towards the fluorescence module 22 by way of the light guide 25.

In the exemplary embodiment shown, the second light source 21 including a wavelength selection device (not shown), for example a monochromator or wavelength filter, serves for passing light through a sample or biological structures in wells of said microplate 10, and a second measuring device 23 (here for example in the form of a photodiode) serves for measuring the absorbance of the sample with regard to the second optical axis 24". The absorbance is calculated by comparing the intensity of the light passing through the sample to the second measuring device 23 with the intensity of the transmitted reference light. If, in contrast, the luminescence of samples is to be detected, the light source can even be omitted and the light signal can be measured by means of photomultiplier tubes for example.

Such light sources are selected for example from a group comprising arc-discharge bulbs, flash bulbs, incandescent bulbs (such as halogen bulbs for example), lasers, laser diodes, and light-emitting diodes (LEDs). The appropriate wavelengths for exciting the fluorescence, and also the appropriate fluorophores and the emission characteristics thereof, are known to a person skilled in the art and will be selected depending on the application. The non-invasive passing of light through cells or cell cultures in order to detect the absorbance, as well as the light sources to be used for this, are also known to a person skilled in the art. Measuring devices 22.3, 23 for detecting at least one integral signal that has been brought about or generated by the light source(s) 21, 22.1 in or on biological structures in the particular wells of the microplate 10 are preferably selected from a group comprising photomultipliers, photodiodes, photodiode arrays and avalanche diodes. The measuring devices 22.3, 23 and light sources 21, 22.1, and/or the optical input and/or output thereof, are preferably coupled by way of light guides 25, such as optical fibres or optical fibre bundles.

The second measuring device 23 of the microplate reader 3 can additionally be used to monitor and/or determine the liquid level in the liquid reservoir of the microplate 10 and/or incubation cassette 1. To this end, the incubation cassette 1 can be moved relative to the second optical axis 24" of the microplate reader 3 such that the second optical axis 24" extends in each case through one of the transparent portions of the incubation cassette 1 and/or microplate 10. The second measuring device 23 can thus also reliably measure the liquid level in the liquid channel of the incubation cassette 1 and/or of the microplate 10. Preferably, the assembly consisting of the light source 21 and the second measuring device 23 is used to measure the absorbance of the liquid in the liquid reservoir of the incubation cassette 1 and/or in the liquid reservoir of the microplate 10.

As described above, the incubation cassette 1 is provided with the transparent portion TA, through which the liquid level in the liquid reservoir of the incubation cassette 1 can be monitored. As an alternative or in addition, in the case of a transparent microplate 10, the liquid level in the liquid reservoir of the microplate 10 can be monitored through the transparent material of said microplate 10. As already mentioned, the assembly consisting of the second light source 21 and the second measuring device 23 is preferably used to measure the absorbance of the liquid in the liquid reservoir of the incubation cassette 1 and/or microplate 10. Further details regarding the absorbance measurement used with preference here will be described in connection with FIGS. 8A, B.

The microplate reader 3 contains for example two injectors 26', 26", wherein a test solution TL is dispensed into the wells of the microplate via a first injector, also called the test solution injector 26', and liquid F is filled into or topped up in the liquid reservoir of the incubation cassette 1 and/or of the microplate 10 via a second injector, also called the liquid injector 26". The liquid reservoir is topped up for example in an automated manner as soon as it is detected, for example by the second measuring device 23 of the microplate reader 3, for example by means of an absorbance measurement, that the level of the liquid F in the liquid reservoir of the incubation cassette 1 and/or of the microplate 10 has fallen below a predefined level. A controller 27, which may be designed for example to control the second light source 21, the second measuring device 23, the movement of the transport support 2 of the microplate reader 3, etc., may also be designed to control the second injector 26" for the automated dispensing of the liquid F into the liquid reservoir of the incubation cassette 1 and/or of the microplate 10. It can thus be ensured that the liquid reservoir of the incubation cassette 1 and/or of the microplate 10 is sufficiently filled with liquid F at all times, even in the case of long-term analyses for example.

The microplate reader 3 additionally comprises an internal or integrated processor 28 or it is designed in such a way as to be able to be connected to an external processor (not shown). Such a processor may thus be a microprocessor integrated in the electronic controller of the microplate reader 3, or a provided Personal Computer.

Figure 7:
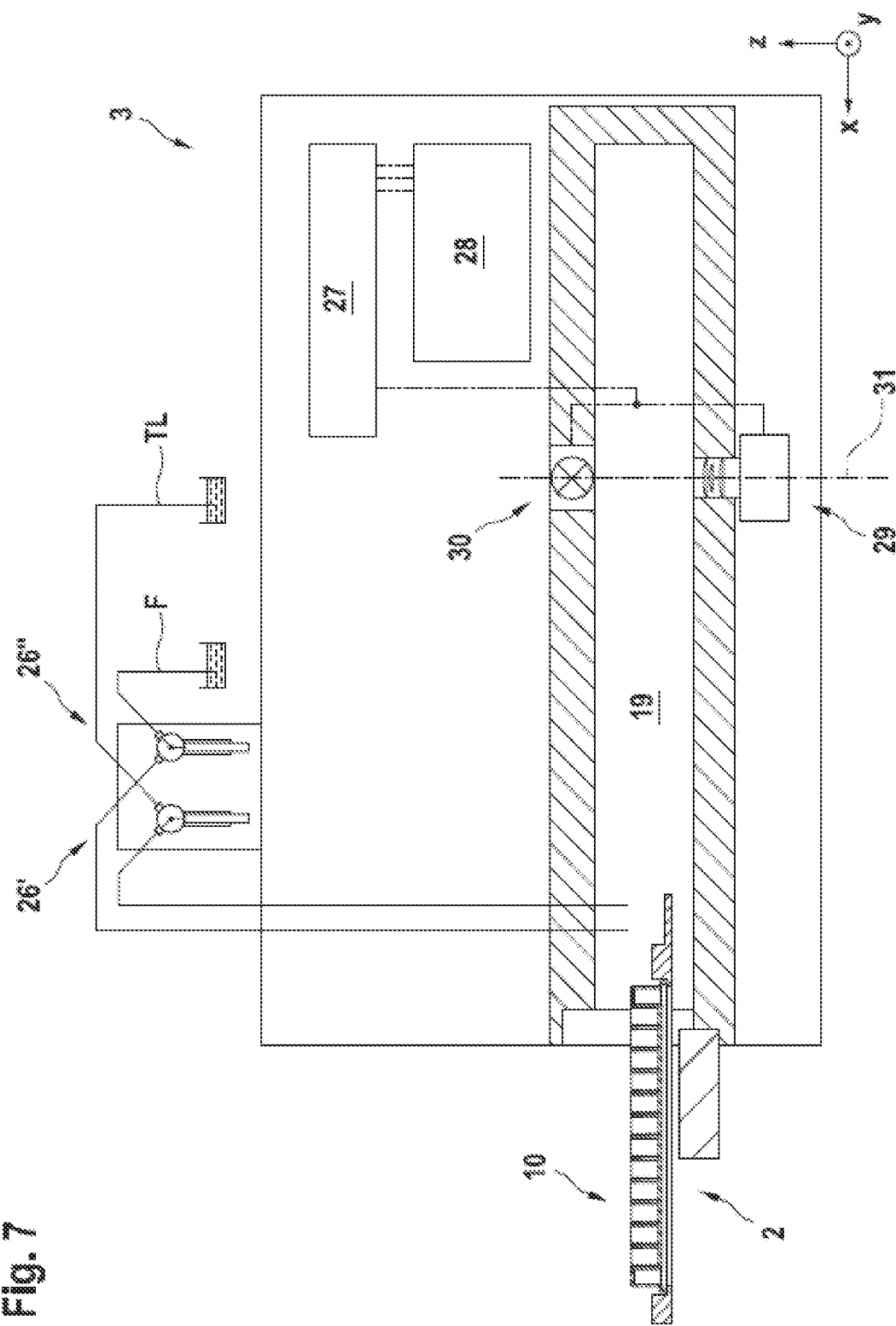
FIG. 7 shows a vertical section through another microplate reader, in which a transport support with a microplate placed thereon is pulled out.

FIG. 7 shows a vertical section through a microplate reader 3 for pushing a microplate 10 (without incubation cassette) into the measurement chamber 19. The microplate 10 may be completely transparent. In the embodiment shown, use is made of an assembly consisting of an imaging module with an optics/lens system 29 and an illumination source 30. Said illumination source 30 illuminates the microplate 10 from above. The imaging module with the optics/lens system 29 captures an image from below through the transparent bottom of a well of the microplate 10. The optics/lens system 29 may be designed to optically increase or reduce the size of images. The microplate reader 3 may have, in addition to the illumination source 30 and the imaging module with the optics/lens system 29, measuring modules as shown in FIG. 6. By way of example, the liquid level can be determined by measuring the absorbance by the liquid.

Figure 8A:
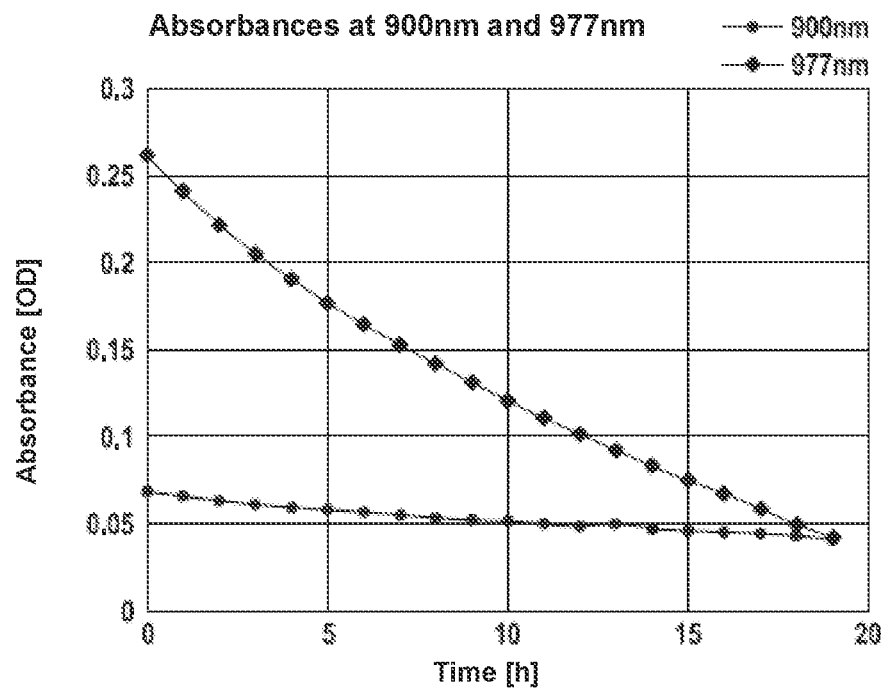
FIGS. 8A, B show curves of an absorbance measurement of the liquid in the liquid reservoir at different wavelengths, in each case plotted as a function of time.

FIGS. 8A, B each show curves of a measured absorbance (at different wavelengths) and a given path length or fill level of a liquid held in the liquid reservoir, in each case plotted as a function of time. FIG. 8A illustrates the measured absorbance of the liquid as a function of time, plotted respectively for a wavelength of 900 nm and 977 nm. As is to be expected, the liquid level decreases over time due to evaporation.

In the case of the absorbance measurement used with preference here, the Beer-Lambert law can be applied according to the equation: A=εcl. The absorbance (A) of the sample can be determined by the product of the extinction coefficient (ε) and the concentration (c) of the sample and the path length (l) through which the sample is measured. In the method, the absorbance peak of the liquid, for example water, at room temperature (977 nm) and a background measurement at 900 nm can be used (see measured values, as plotted in FIG. 8A). The difference in optical density (i.e. 977 nm-900 nm) can be divided by 0.18, which is the optical density of water at 1 cm. The result of the above calculation gives the path length or the liquid level of the liquid in the liquid reservoir.

Figure 8B:
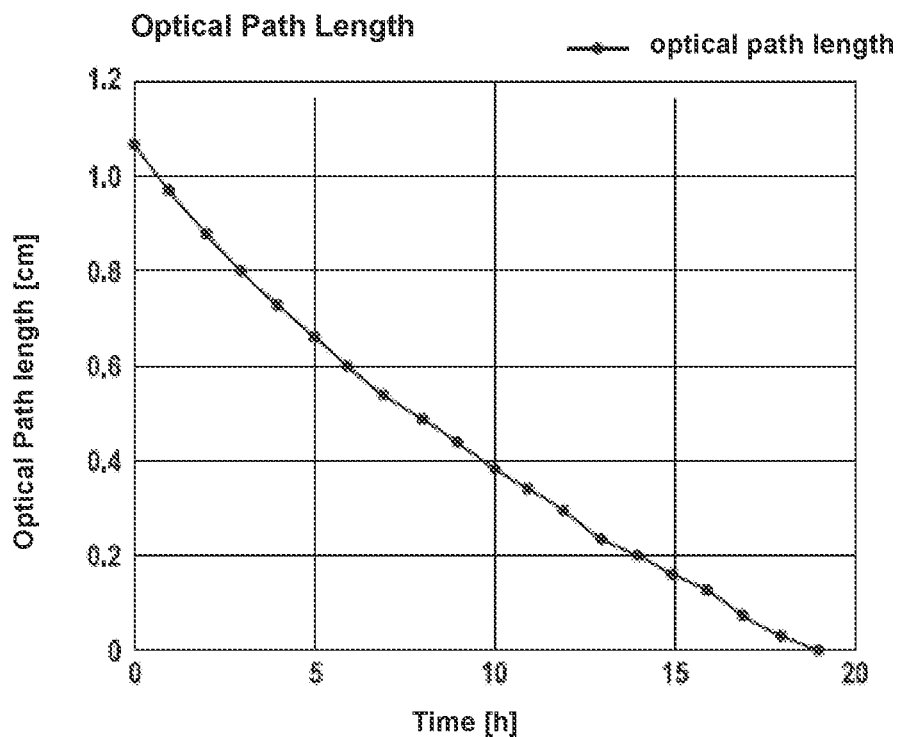

By applying the Lambert-Beer law, the path length (i.e. fill level or liquid level) can be determined by measuring the liquid (aqueous sample) at 900 nm, in order to obtain an absorbance baseline, and measuring it at 977 nm, in order to obtain the specific absorbance of the liquid (aqueous sample), by applying the equation:

$$\text{Fill level} = \frac{A_{977} - A_{900}}{A_{water} \text{cm}^{-1}}$$

where:
$A_{977}$→absorbance of the aqueous sample at 977 nm
$A_{900}$→absorbance of the aqueous sample at 900 nm
$A_{water}$→$A_{977}$-$A_{900}$ water in a 1 cm cuvette By applying the equation, the fill level or liquid level of the liquid in the liquid reservoir is determined, as plotted in FIG. 8B. In the example shown, a drop in fill level from initially around 1.1 cm to 0 cm is measured over approximately 18 hours. By precisely measuring the fill level in this way, the liquid in the liquid reservoir can be topped up in good time, for example at a measured fill level of 0.6 cm, 0.4 cm, 0.2 cm, etc.

Figure 9A:
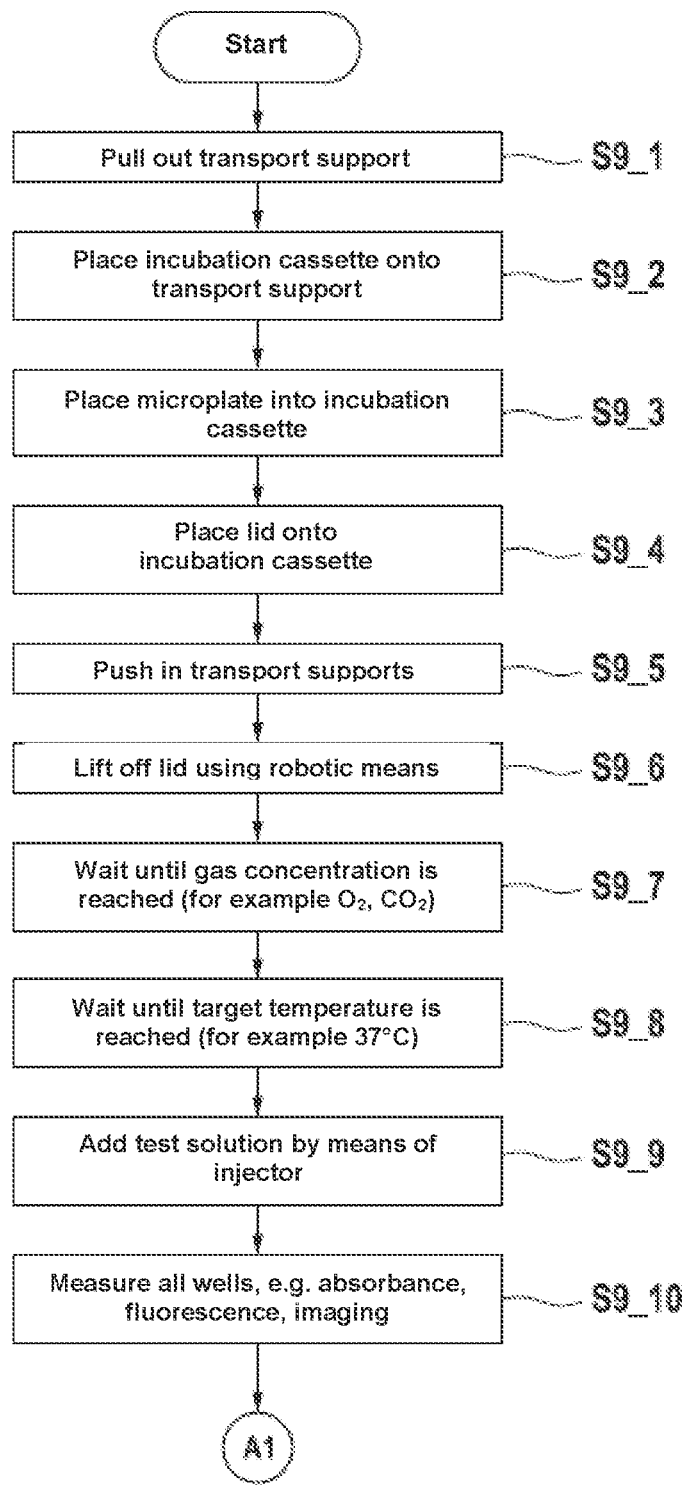
FIGS. 9A, B show a flowchart of a method for reducing liquid evaporation from wells of a microplate placed in an incubation cassette.
Figure 9B:
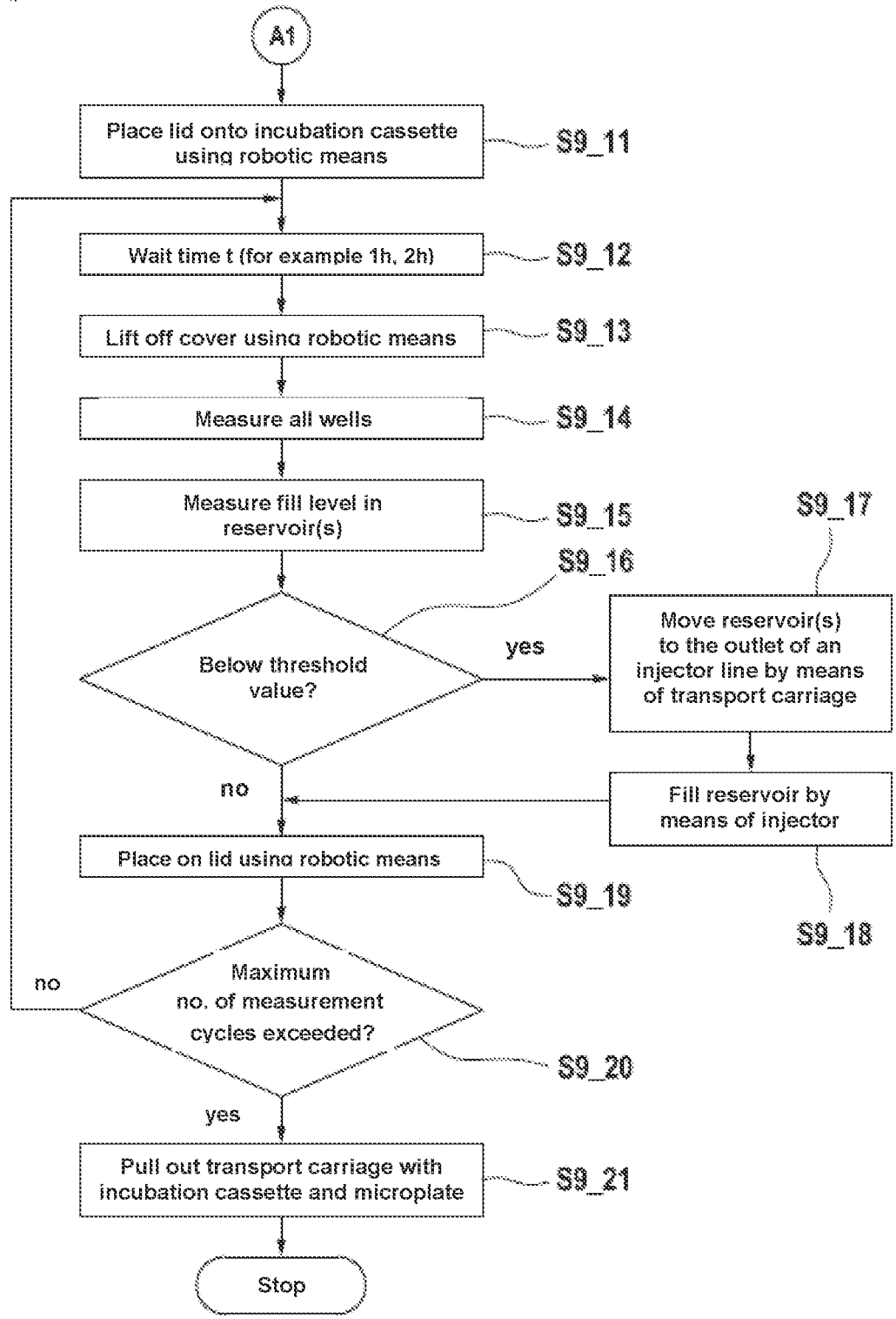
Figure 10A:
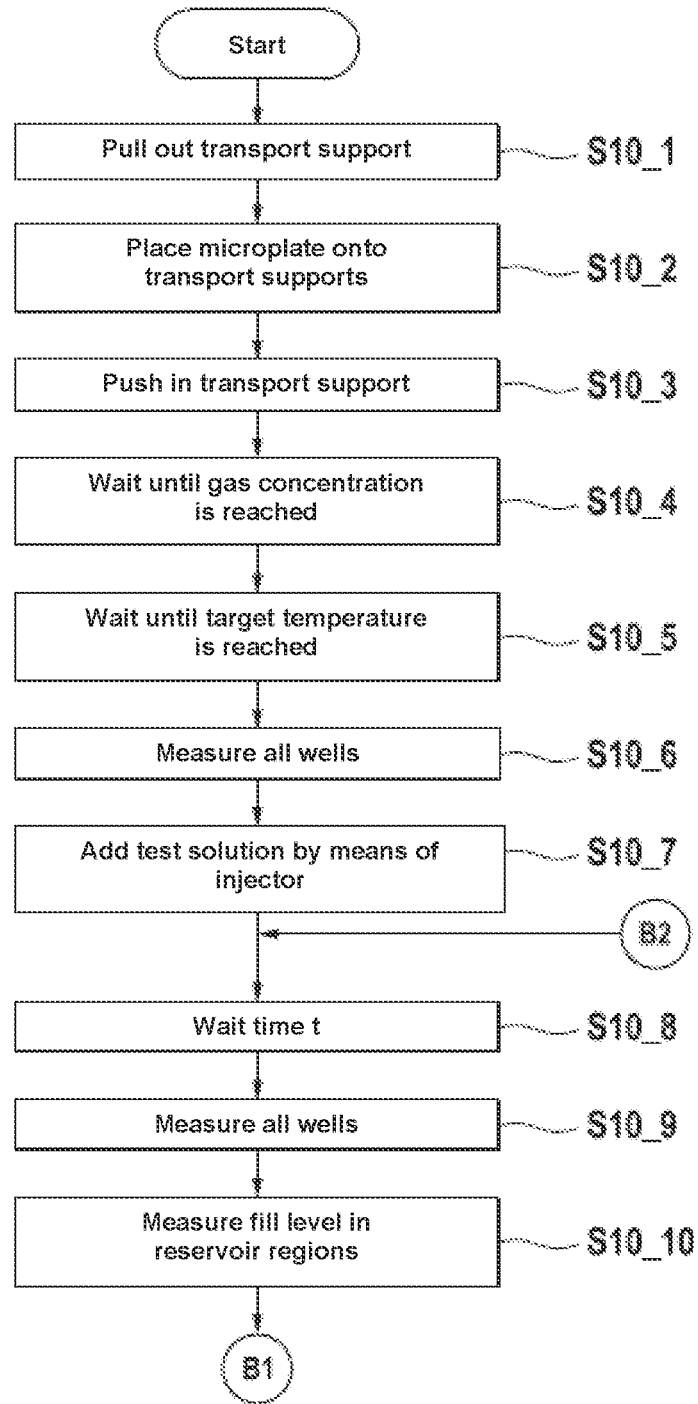
FIGS. 10A, B show a flowchart of a method for reducing liquid evaporation from wells of a microplate.
Figure 10B:
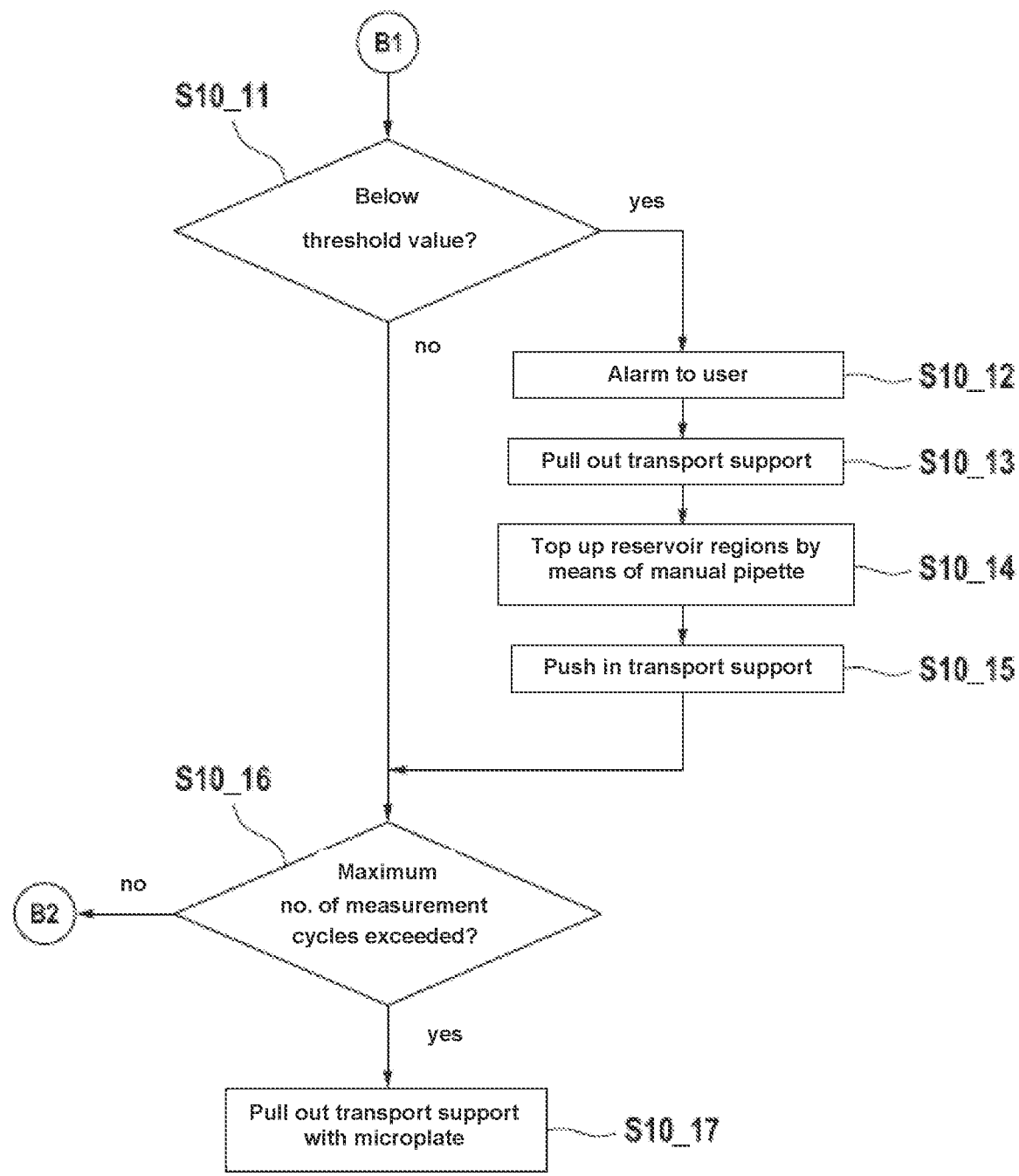

FIGS. 9A, B show a flowchart of a method for reducing liquid evaporation from wells of a microplate placed in an incubation cassette. FIGS. 10A, B show a flowchart of a method for reducing liquid evaporation from wells of a microplate.

With regard to the flowchart shown in FIGS. 9A, B, reference is made to the microplate readers shown respectively in FIGS. 6 and 7, into which an incubation cassette is pushed, a microplate in turn being placed in said incubation cassette (FIG. 6), or simply a microplate (without incubation cassette) is pushed into the microplate reader (FIG. 7). The method begins with a step S9_1, in which the transport support of the microplate reader is pulled out. In a step S9_2, the incubation cassette is placed onto the transport support. However, the incubation cassette may also be permanently placed thereon. In a step S9_3, the microplate is placed into the incubation cassette. In a step S9_4, a lid is then placed onto the incubation cassette. The transport support with the incubation cassette thus prepared is pushed into the microplate reader in a step S9_5. In the microplate reader, the lid is lifted off using robotic means (step S9_6). In the microplate reader, the gas concentration is also measured (for example the concentration of $O_2$, $CO_2$, etc.), and in a step S9_7 there is a wait until a predetermined gas concentration is reached. In the microplate reader, the temperature is also measured, and in a step S9_8 there is a wait until a predetermined target temperature is reached, for example 37° C. As soon as the predetermined gas concentration and/or target temperature is reached, in a step S9_9 the test solution is added to predetermined, substance-containing wells of the microplate by means of an injector. However, the test solution may also be added at an earlier point in time, for example outside of the microplate reader, that is to say before the microplate is pushed into the microplate reader. Furthermore, in this step, the liquid can be added to the liquid reservoir of the incubation cassette and/or of the microplate. However, the liquid may also be added earlier, for example outside of the microplate reader, that is to say before the incubation cassette with the microplate is pushed into the microplate reader.

In a step S9_10, the samples in the wells are measured by measurement methods, such as for example absorbance, fluorescence, imaging, etc. Then, in a step S9_11, the lid is placed onto the incubation cassette. This reduces the evaporation of liquid from the wells of the microplate. In a step S9_12, there is a wait for a predetermined time interval, for example 1h, 2 h, etc. Once the predetermined time interval has elapsed, the lid is lifted off using robotic means in a step S9_13. In a step S9_14, the samples in the respective wells are measured. Then, in a step S9_15, the fill level of the liquid in the liquid reservoir of the incubation cassette and/or in the liquid reservoir of the microplate is measured. In a step S9_16 it is determined, based on the result of the fill level measurement, whether the fill level has or has not fallen below a predetermined threshold value.

If it is determined in step S9_16 that the fill level has fallen below the threshold value (yes), the method continues at a step S9_17, in which the liquid reservoir of the incubation cassette and/or the liquid reservoir of the microplate is moved by means of the transport support to an outlet of an injector line of an injector in order to add liquid. As soon as this position is reached, the liquid reservoir in question is filled or topped up by the injector (step S9_18). The method then continues at a step S9_19, which will be described below.

If it is determined in step S9_16 that the fill level has not fallen below the threshold value (no), the method continues at step S9_19, in which the lid is placed back onto the incubation cassette using robotic means. In a subsequent step S9_20, it is determined whether a predetermined maximum number of measurement cycles has been exceeded. If it is determined in step S9_20 that the maximum number of measurement cycles has not been exceeded (no), the method returns to step S9_12. If it is determined in step S9_20 that the maximum number of measurement cycles has been exceeded (yes), the method continues at step S9_21, in which the transport support with the incubation cassette and the microplate placed therein is pulled out of the microplate reader. After this, the method can be ended.

It should be mentioned that the order of the steps in the flowchart can be changed. In addition, the method described in the flowchart is not to be regarded as being limited to the incubation cassette, the microplate placed therein and the lid placed onto the incubation cassette, as described above by way of example. Besides the described incubation cassette with the lid placed thereon, use can also be made for example of an incubation cassette without a lid. In this case, there is no need for robotic means for lifting off the lid. In this case, it is possible that the microplate contains no reservoir(s). In this case, the measurement chamber of the microplate reader should be as small as possible. Besides the automated topping-up of the reservoir by the injector, as described here, the topping-up may also take place manually.

With regard to the flowchart shown in FIGS. 10A, B, reference is made to the microplate readers shown respectively in FIGS. 6 and 7, into which an incubation cassette is pushed, a microplate in turn being placed in said incubation cassette (FIG. 6), or simply a microplate (without incubation cassette) is pushed into the microplate reader (FIG. 7). The method begins with a step S10_1, in which the transport support of the microplate reader is pulled out. In a step S10_2, the microplate is placed onto the transport support. In a step S10_3, the transport support with the microplate placed thereon is pushed into the microplate reader. In the microplate reader, the gas concentration is measured (for example the concentration of $O_2$, $CO_2$, etc.), and in a step S10_4 there is a wait until a predetermined gas concentration is reached.

In the microplate reader, the temperature is also measured, and in a step S10_5 there is a wait until a predetermined target temperature is reached. As soon as the predetermined gas concentration and/or target temperature is reached, in a step S10_6 the samples in the respective wells of the microplate are measured by measurement methods, such as for example absorbance, fluorescence, imaging, etc., in order to generate a "blank" value for the subsequent measurements. In a step S10_7, test solution is added to predetermined, substance-containing wells of the microplate by means of an injector. However, the test solution may also be added at an earlier point in time, for example outside of the microplate reader, that is to say before the microplate is pushed into the microplate reader. Furthermore, in this step, the liquid can be added to the liquid reservoir of the microplate. However, the liquid may also be added earlier, for example outside of the microplate reader, that is to say before the microplate is pushed into the microplate reader. In a step S10_8, there may be a wait for a predetermined time t. In a step S10_9, the samples provided with the test solution in the respective wells are measured. Then, in a step S10_10, the fill level of the liquid in the liquid reservoir of the microplate is measured. In a step S10_11 it is determined, based on the result of the aforementioned measurement, whether the fill level has or has not fallen below a predetermined threshold value.

If it is determined in step S10_11 that the fill level has fallen below the threshold value (yes), the method continues at a step S10_12, in which an alarm can be output to a user of the microplate reader. In a step S10_13, the transport support is pulled out of the microplate reader. As soon as the transport support has been pulled out of the microplate reader, in a step S10_14 the liquid reservoir of the microplate is topped up with liquid, for example manually by means of a manual pipette. The transport support is then pushed into the microplate reader (step S10_15). The method then continues at a step S10_16, which will be described below.

If it is determined in step S10_11 that the fill level has not fallen below the threshold value (no), the method continues at step S10_16, in which it is determined whether a predetermined maximum number of measurement cycles has been exceeded.

If it is determined in step S10_16 that the maximum number of measurement cycles has not been exceeded (no), the method returns to step S10_8. If it is determined in step S10_16 that the maximum number of measurement cycles has been exceeded (yes), the method continues at step S10_17, in which the transport support with the microplate placed thereon is pulled out of the microplate reader. After this, the method can be ended.

It should be mentioned that the order of the steps in the described flowchart can be changed. In addition, the method described in the flowchart is not to be regarded as being limited to the microplate without a lid placed thereon, as described above by way of example. Besides the described microplate without a lid placed thereon, use can also be made for example of a microplate with a lid. The microplate is provided with at least one reservoir. When using a microplate without a lid placed thereon, there is no need for robotic means in the microplate reader for lifting off the lid. Also in this case, the measurement chamber of the microplate reader should be as small as possible. The topping-up of the reservoir may take place by means of the injector or manually.

All the described flowcharts are to be regarded as examples and serve to explain the invention. Method steps described herein are not to be limited to the orders described. The respective orders can be changed. Method steps may differ from the orders described.

Identical reference signs in the figures denote identical or at least similar features, even if these are not described in detail in each case.

| Reference signs | |
|---|---|
| 1 | incubation cassette |
| 2 | transport support |
| 3 | microplate reader |
| 4 | frame, incubation frame |
| 5 | central first opening |
| 6 | inner wall |
| 7 | support surface of 4 |
| 8 | outer wall |
| 9 | liquid reservoir |
| 10 | microplate |
| 11 | lid |
| 11', 11" | lid |
| 12 | web of microplate |
| 13 | magnetizable surface |
| 14 | intermediate bottom |
| 15 | lowered region |
| 16' | edge of 11' |
| 16" | edge of 11" |
| 17 | cutout |
| 18 | circumferential web of incubation cassette |
| 19 | measurement chamber |
| 21 | second light source |
| 22 | fluorescent module |
| 22.1 | first light source |
| 22.2 | semi-transparent or dichroic mirror |
| 22.3 | first measuring device |
| 23 | second measuring device |
| 24' | first optical axis |
| 24" | second optical axis |
| 25 | light guide |

| Reference signs | |
|---|---|
| 26' | first injector |
| 26" | second injector |
| 27 | controller |
| 28 | processor |
| 29 | imaging module with optics/lens system |
| 30 | illumination source |
| 31 | optical axis |
| 32 | panel |
| F | liquid |
| TA | transparent portion |
| TL | test solution |

What is claimed is:

1. A microplate reader comprising:
a measurement chamber;
a transport support which is configured to be inserted into the measurement chamber, the transport support having a bearing surface holding an incubation cassette for reducing liquid evaporation from wells of a microplate; wherein the incubation cassette comprises a frame for receiving the microplate, wherein the frame comprises a central opening which is surrounded by an inner wall, dimensions of which allow for placement of the microplate therein, and wherein the frame comprises an outer wall which extends substantially parallel to the inner wall and which adjoins the inner wall via an intermediate bottom such that a liquid reservoir for holding a liquid is formed by the inner wall, the outer wall and the intermediate bottom, said liquid reservoir surrounding the central opening wherein at least a portion of the incubation cassette that forms the liquid reservoir is provided with at least one transparent portion;
a first measuring device located in the microplate reader for optically assaying or analyzing a content of the wells of the microplate in the measurement chamber;
a second measuring device located in the microplate reader for monitoring and/or determining a liquid level in the liquid reservoir of the incubation cassette in the measurement chamber; and
a controller configured to control the first measurement device, the second measurement device and movement of the transport support such that either the first measuring device is used for assaying the content of the wells of the microplate or the second measurement device is used for determining the liquid level in the liquid reservoir.

2. The microplate reader according to claim 1 wherein the second measuring device utilizes absorbance of the liquid for determining an optical path length related to the liquid level in the liquid reservoir.

3. The microplate reader according to claim 2, wherein the second measuring device comprises a second light source arranged along a second optical axis with the second measuring device and the incubation cassette is configured to be moved in the measurement chamber relative to the second optical axis such that the second optical axis extends through the at least one transparent portion of the incubation cassette.

4. The microplate reader according to claim 3, wherein the second light source comprises a wavelength selection device.

5. The microplate reader according to claim 1, wherein the first measuring device uses absorbance, fluorescence and/or luminescence measurements from a reflected or transmitted light beam for assaying or analyzing the content of the wells of the microplate.

6. The microplate reader according to claim 5, wherein the first measuring device comprises a first light source arranged along a first optical axis with the first measuring device and the incubation cassette is configured to be moved relative to the first optical axis in the microplate reader such that the first optical axis extends through one of the wells of the microplate.

7. The microplate reader according to claim 6 wherein the first light source comprises a wavelength selection device.

8. The microplate reader according to claim 3, wherein the first optical axis and the second optical axis extend through the measurement chamber and are arranged parallel to another.

9. The microplate reader according to claim 3, wherein the first optical axis and the second optical axis are arranged perpendicular to a movement direction of the transport support.

10. The microplate reader according to claim 3, wherein the liquid reservoir of the incubation cassette is configured to be filled with liquid manually.

11. The microplate reader according to claim 3, wherein the microplate reader comprises a first injector controlled by the controller, and wherein the liquid reservoir of the incubation cassette is configured to be filled with liquid in an automated manner by the first injector as soon as it is detected that the liquid level in the liquid reservoir is below a predefined liquid level.

12. The microplate reader according to claim 11, wherein the controller moves the liquid reservoir of the incubation cassette by means of the transport support to an outlet of the first injector in order to add liquid and as soon as this position is reached, the controller controls the first injector to fill the liquid in the liquid reservoir of the incubation cassette.

13. The microplate reader according to claim 12, comprising a second injector, wherein the second injector is configured to dispense a test solution into the wells of the microplate.

14. A microplate reader comprising:
a measurement chamber;
a transport support which is configured to be inserted into the measurement chamber, the transport support having a bearing surface holding an incubation cassette for reducing liquid evaporation from wells of a microplate;
wherein the incubation cassette comprises a frame for receiving the microplate, wherein the frame comprises a central opening which is surrounded by an inner wall, dimensions of which allow for placement of the microplate therein, and wherein the frame comprises an outer wall which extends substantially parallel to the inner wall and which adjoins the inner wall via an intermediate bottom such that a liquid reservoir for holding a liquid is formed by the inner wall, the outer wall and the intermediate bottom, said liquid reservoir surrounding the central opening wherein at least a portion of the incubation cassette that forms the liquid reservoir is provided with at least one transparent portion;
a first measuring device for optically assaying or analyzing a content of the wells of the microplate,
a second measuring device to monitor and/or determine a liquid level in the liquid reservoir of the incubation cassette;
a first injector for filling the liquid reservoir; and
a controller configured to control the first measurement device, the second measurement device, the first injector and movement of the transport support such that the first measuring device is used for assaying the content of the wells of the microplate or the second measurement device is used for determining the liquid level in the liquid reservoir or the first injector is used for filling the liquid reservoir.

15. The microplate reader according to claim 14 further comprising a second injector configured to dispense a test solution into the wells of the microplate.

16. The microplate reader according to claim 14 wherein the second measuring device utilizes absorbance of the liquid for determining an optical path length or the liquid level in the liquid reservoir.

17. The microplate reader according to claim 16, wherein the second measuring device comprises a second light source arranged along a second optical axis with the second measuring device and the incubation cassette is configured to be moved relative to the second optical axis in the microplate reader such that the second optical axis extends through the at least one transparent portion of the incubation cassette.

18. The microplate reader according to claim 17, wherein the first measuring device uses absorbance measurements, fluorescence measurements, and/or luminescence measurements from a reflected or transmitted light beam for assaying or analyzing the content of the wells of the microplate.

19. The microplate reader according to claim 18, wherein the first measuring device comprises a first light source arranged along a first optical axis with the first measuring device and the incubation cassette is configured to be moved relative to the first optical axis in the microplate reader such that the second optical axis extends through one of the wells of the microplate.

* * * * *